US008882777B2

(12) United States Patent
Heavener et al.

(10) Patent No.: US 8,882,777 B2
(45) Date of Patent: Nov. 11, 2014

(54) INDICATOR DEVICE FOR USE WITH A SURGICAL GUIDE INSTRUMENT

(75) Inventors: Jackson R. Heavener, Warsaw, IN (US); Shawn E. McGinley, Fort Wayne, IN (US); James S. Collins, Fort Wayne, IN (US); Kathleen J. Radford, Winona Lake, IN (US); James E. Grimm, Winona Lake, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 1495 days.

(21) Appl. No.: 11/687,176

(22) Filed: Mar. 16, 2007

(65) Prior Publication Data

US 2007/0219559 A1 Sep. 20, 2007

Related U.S. Application Data

(60) Provisional application No. 60/783,244, filed on Mar. 17, 2006.

(51) Int. Cl.
*A61F 5/00* (2006.01)
*B26D 7/00* (2006.01)
*B26D 7/27* (2006.01)
*B26D 7/28* (2006.01)
*A61B 19/00* (2006.01)
*A61B 17/17* (2006.01)
*A61B 18/20* (2006.01)

(52) U.S. Cl.
CPC ............. *A61B 17/1764* (2013.01); *A61B 19/52* (2013.01); *A61B 19/2203* (2013.01); *A61B 2018/2025* (2013.01)
USPC .............................. 606/87; 83/520; 83/522.15

(58) Field of Classification Search
CPC ...................................................... A61B 17/15
USPC ......... 83/821–829, 522.15–522.16, 520–521; 606/86 R, 87–89, 96–98; 408/16, 72; 362/89
See application file for complete search history.

(56) References Cited

U.S. PATENT DOCUMENTS

| | | | | |
|---|---|---|---|---|
| 3,854,836 A * | 12/1974 | Weissman | .................. | 408/14 |
| 5,426,687 A * | 6/1995 | Goodall et al. | .............. | 378/206 |
| 5,571,110 A * | 11/1996 | Matsen et al. | ................... | 606/88 |
| 5,891,158 A * | 4/1999 | Manwaring et al. | .......... | 606/130 |
| 6,514,259 B2 * | 2/2003 | Picard et al. | .................... | 606/88 |
| 6,755,107 B2 * | 6/2004 | Peot et al. | ....................... | 83/478 |
| 7,510,557 B1 * | 3/2009 | Bonutti | ........................ | 606/86 R |
| 2002/0170404 A1 * | 11/2002 | Peot et al. | ....................... | 83/478 |
| 2004/0153066 A1 | 8/2004 | Coon et al. | | |
| 2004/0182215 A1 * | 9/2004 | Ushiwata et al. | .......... | 83/522.15 |
| 2005/0261555 A1 * | 11/2005 | Guzman et al. | ............... | 600/204 |
| 2006/0030850 A1 * | 2/2006 | Keegan et al. | .................. | 606/60 |
| 2007/0217878 A1 * | 9/2007 | Byrd | .............................. | 408/16 |

\* cited by examiner

*Primary Examiner* — Andrew Yang
*Assistant Examiner* — Diana S Jones
(74) *Attorney, Agent, or Firm* — Norton Rose Fulbright Canada LLP

(57) ABSTRACT

Instruments for use in resecting, reshaping, and preparing the end of a bone to receive an implant. The instruments may be equipped with indicator devices in the form of light-emitting devices to project an indicator onto the bone. Examples of such instruments may be a cut guide equipped with a built-in cut plane indicator device and a cut plane indicator device for use with existing cut guides. The cut plane indicator device may provide a visual indication or cue on a surface of the bone indicating where the cut plane of the cut guide will intersect the bone.

15 Claims, 7 Drawing Sheets

INDICATOR DEVICE FOR USE WITH A SURGICAL GUIDE INSTRUMENT

CROSS REFERENCE TO RELATED APPLICATIONS

This application claims the benefit under Title 35, U.S.C. §119(e) of U.S. Provisional Patent Application Ser. No. 60/783,244, entitled CUT PLANE INDICATOR DEVICE FOR USE WITH A CUT GUIDE, filed Mar. 17, 2006, the disclosure of which is hereby expressly incorporated herein by reference.

BACKGROUND

The present disclosure relates to guide instruments for use in preparing the surface of a bone to receive an implant and, more particularly, to a light-emitting device for indicating a location on the bone surface.

Orthopaedic procedures for the replacement of all, or a portion of, a patient's joint typically require resecting and/or reshaping of the ends of the bones of the joint. For instance, total knee replacement procedures typically involve resecting the distal end of the femur and the proximal end of the tibia prior to implanting the prosthetic components.

Guide instruments, such as cut guides, for example, have been developed to guide a resection instrument, such as a saw, for example, in making cuts on the femur and the tibia. Conventional cut guides are often in the form of blocks having slots therein for receiving and guiding the saw. In use, the block is positioned against the bone with the help of positioning and alignment equipment. Once the cut block is properly positioned, the resection instrument is inserted through the cut slot of the block and into the bone.

SUMMARY

The present disclosure provides instruments for use in resecting, reshaping, and preparing the end of a bone to receive an implant. The instruments may be equipped with indicator devices in the form of light-emitting devices to project an indicator onto the bone. Examples of such instruments may be a cut guide equipped with a built-in cut plane indicator device and a cut plane indicator device for use with existing cut guides. The cut plane indicator device may provide a visual indication or cue on a surface of the bone indicating where the cut plane of the cut guide will intersect the bone.

In one form, the present disclosure provides a guidance system for guiding a surgical procedure performed on an anatomical structure, the guidance system including a surgical guide instrument including at least one guide surface, the at least one guide surface extending along a guide direction; and a light-emitting device securable to the guide instrument in a secured position such that an output of the light-emitting device is projected along the guide direction.

In another form thereof, the present disclosure provides a guidance system for guiding a surgical procedure performed on an anatomical structure, the guidance system including guidance means for guiding a surgical instrument relative to a guide direction; and indication means for providing an indicator on the anatomical structure corresponding to the guide direction.

In yet another form thereof, the present disclosure provides a method of performing an orthopaedic surgical procedure on an anatomical structure, including providing a guide instrument including at least one guide surface, the at least one guide surface extending along a guide direction; providing a light-emitting device associated with the guide instrument; and projecting an indicator from the light-emitting device onto the anatomical structure corresponding to the guide direction.

BRIEF DESCRIPTION OF THE DRAWINGS

The above mentioned and other features of this disclosure, and the manner of attaining them, will become more apparent and will be better understood by reference to the following description of embodiments of the disclosure taken in conjunction with the accompanying drawings, wherein.

Figure 1:
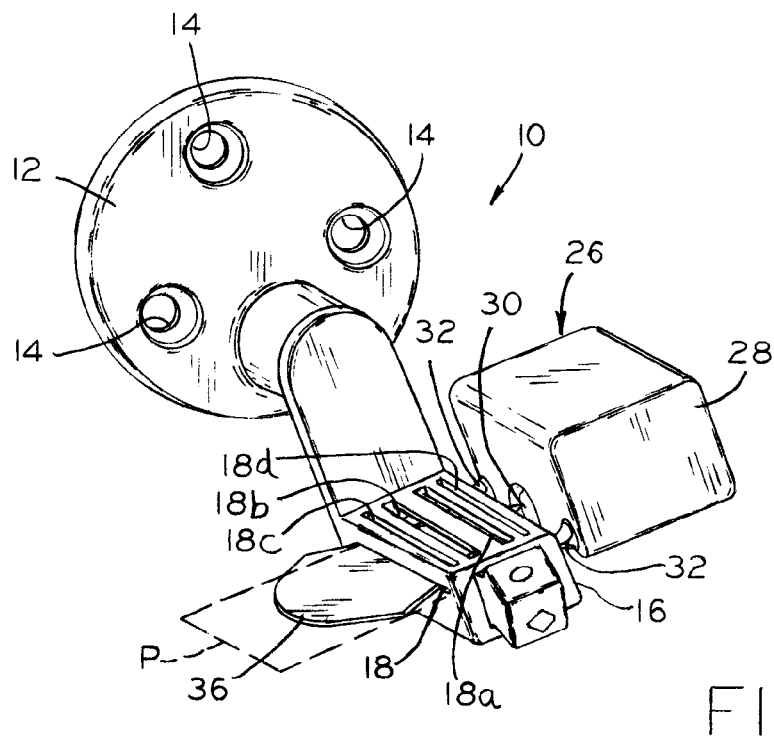
FIG. 1 is a perspective view of a cut guide and cut plane indicator device according to one embodiment of the present disclosure.
Figure 2:
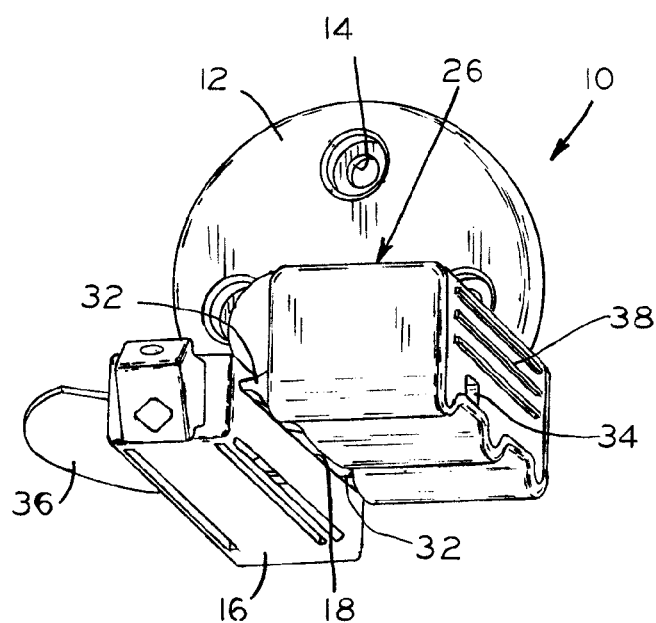
FIG. 2 is another perspective view of the cut guide and cut plane indicator device of FIG. 1.

Corresponding reference characters indicate corresponding parts throughout the several views. Although the drawings represent embodiments of the present disclosure, the drawings are not necessarily to scale and certain features may be exaggerated in order to better illustrate and explain the present disclosure. Although the exemplifications set out herein illustrate embodiments of the disclosure, the embodiments disclosed below are not intended to be exhaustive or to be construed as limiting the scope of the disclosure to the precise forms disclosed.

DETAILED DESCRIPTION

Referring to FIGS. 1-9, an assembly of cut guide 10 and cut plane indicator device 26 according to one embodiment of the present disclosure will now be described. As illustrated in FIGS. 1-6, cut guide 10 generally includes adapter portion 12 and cut block 16 extending outwardly from adapter portion 12. Cut guide 10 may be operably coupled to a computer assisted surgery (CAS) system, for example, a robotic surgical system or haptic device, such as the BRIGIT system (Bone Resection Instrument Guidance System by Intelligent Telemanipulator), available from Zimmer, Inc. of Warsaw, Ind., and described in U.S. patent application Ser. No. 11/610,728, entitled AN IMAGELESS ROBOTIZED DEVICE AND METHOD FOR SURGICAL TOOL GUIDANCE, filed Dec. 14, 2006, assigned to the assignee of the present application, the disclosure of which is hereby expressly incorporated herein by reference. Accordingly, adapter portion 12 may be configured to be coupled to the BRIGIT system and may include fastener receiving holes 14 through which fasteners (not shown) may extend to secure cut guide 10 to an arm of the BRIGIT system device. Alternatively, cut guide 10 may be adapted and configured to couple with any image-guided system, any imageless CAS system, any non-robotic system, or any robotic system. Moreover, cut guide 10 may be in the form of a more traditional, manually operated cut guide, such as cut guide 110 illustrated in FIG. 12 and discussed below, or in the form of the cut guides disclosed in U.S. Patent Application Publication No. 2004/0153066, entitled APPARATUS FOR KNEE SURGERY AND METHODS OF USE, filed on Feb. 3, 2003, assigned to the assignee of the present application, the disclosure of which is hereby expressly incorporated herein by reference.

Figure 3:
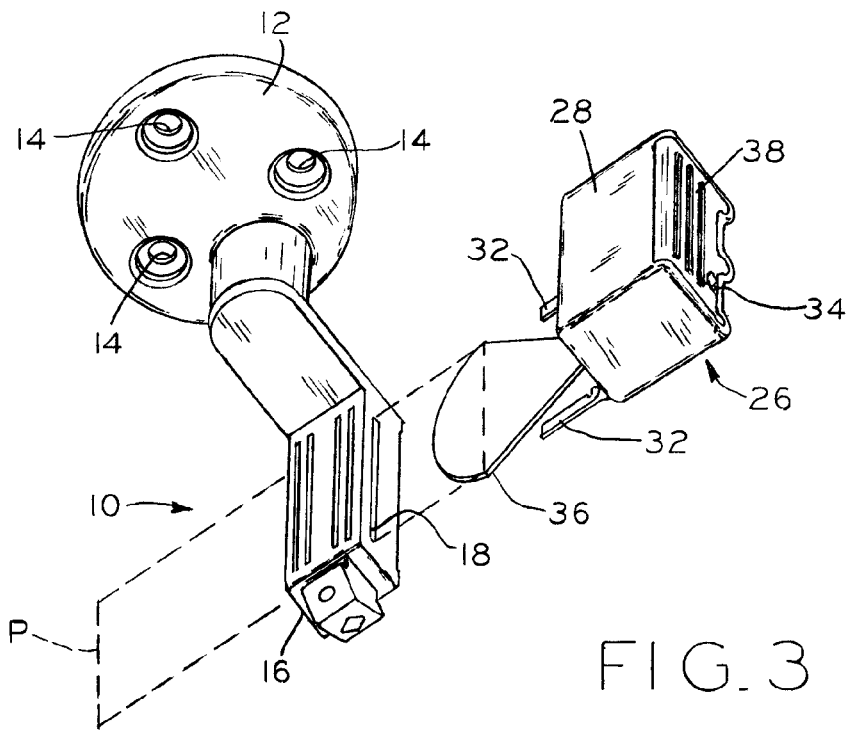
FIG. 3 is an exploded view of the cut guide and cut plane indicator device of FIG. 1.
Figure 4:
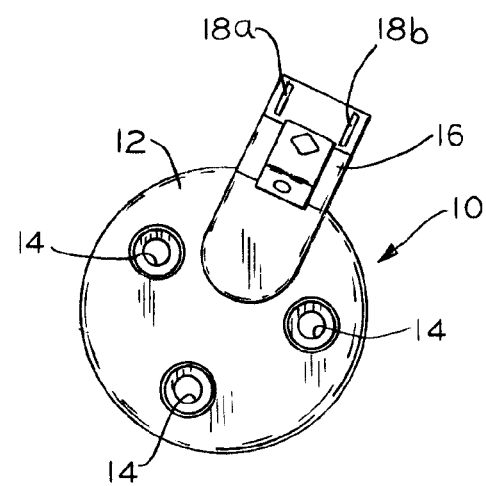
FIG. 4 is an end view of the cut guide of FIG. 1.
Figure 5:
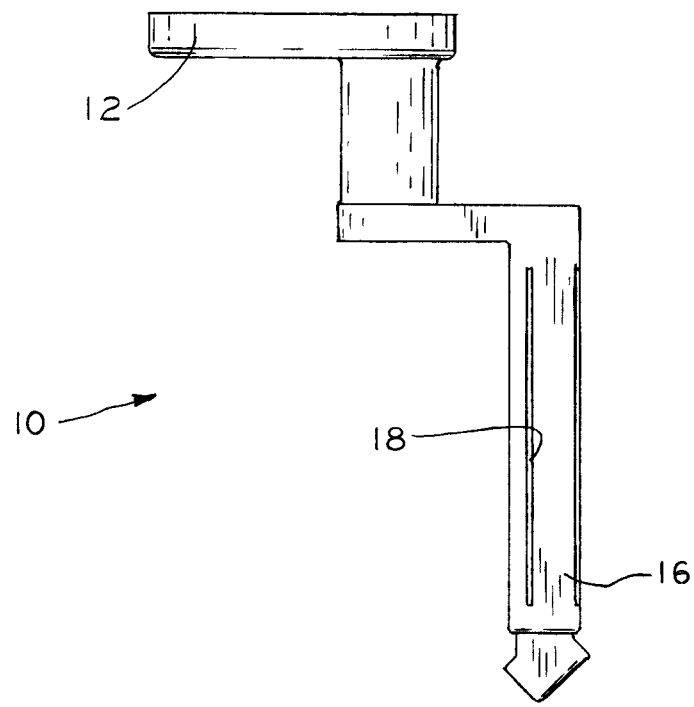
FIG. 5 is a side view of the cut guide of FIG. 4.
Figure 6:
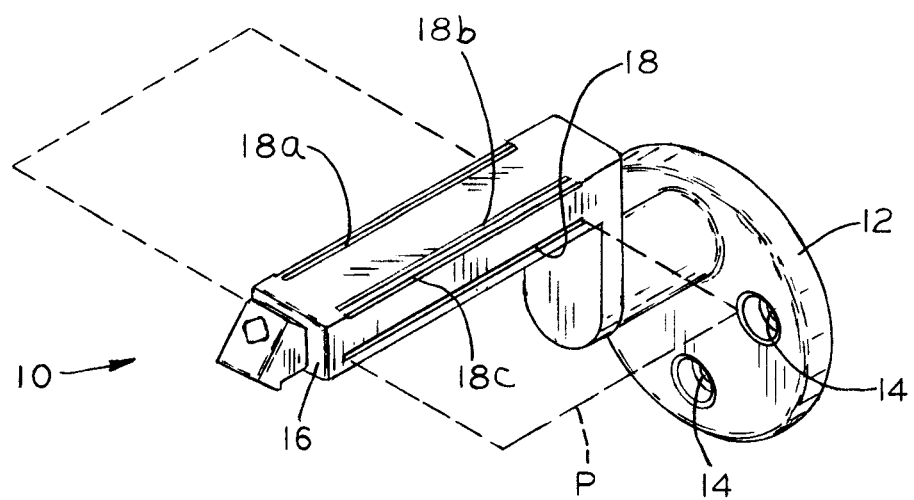
FIG. 6 is another perspective view of the cut guide of FIG. 4.

Referring to FIGS. 1-6, cut guide 10 may include a plurality of cut guide slots 18, 18a-18d extending through cut block 16 at various angles. Each of cut guide slots 18, 18a-18d extends along and defines a cut guide plane, which is exemplified with respect to cut guide slot 18 as cut guide plane P (FIGS. 1, 3, and 6). Cut guide slots 18, 18a-18d are configured to receive therethrough a cutting or resection instrument, such as a saw, and to guide the cutting instrument along cut guide plane P. Alternatively, any surface of cut guide 10 may provide a cutting guide, such as the top surface of cut guide 10, for example, to define cut guide plane P.

Referring now to FIGS. 1-3 and 7-9, cut plane indicator device 26 generally includes body 28, laser or light-emitting indicator source 30 disposed within body 28, and paddles or tabs 32 extending outwardly from body 28. Body 28 defines a battery compartment (not shown) accessible by battery compartment door 38. The battery compartment may house a battery (not shown), which is operably coupled to laser 30 to provide power thereto. Alternatively, laser 30 may be electrically coupled to the CAS system, such as by a power wire/cord, thereby deriving power from the CAS system. Cut plane indicator device 26 also includes on/off switch 34 which couples the power source to laser 30 and controls the flow of power to laser 30. As illustrated and described in further detail below, laser 30 may be a line-producing laser adapted to project a line 40 (FIGS. 10 and 11) onto a surface. Laser 30 produces a beam of light (not shown) and includes a lens (not shown), which is adapted to refract the laser beam to produce laser output 36. Laser output 36 projects line 40 (FIGS. 10 and 11) onto a surface located distant from laser 30. In one form, laser output 36 is generally fan-shaped such that line 40 produced on a distant surface generally extends across a wide portion of the surface to ensure that line 40 provides sufficient guidance during a surgical procedure. Laser 30 may be any suitable line-producing laser that does not cause biological damage to the surface on which line 40 is projected. In one embodiment, laser 30 may include output 36 having two perpendicular lines 40. The two perpendicular lines may provide a resection line, e.g., a horizontal line, and an alignment line, e.g., a vertical line, such that the alignment line aligns with a mechanical axis of a bone, for example. Laser 30 may include any one of a plurality of lenses which are adapted to refract the laser beam to produce laser output 36. For example, one exemplary lens may provide output 36 with reference lines. In another exemplary embodiment, a lens may provide extreme dimensional limits of a proposed prosthesis, i.e., a medial-lateral dimension and an anterior-posterior dimension of the prosthesis, such that a surgeon may preoperatively assess the suitability of the prosthesis. In other embodiments, a lens may provide a circle output, a square output, or an outline of a proposed prosthesis. In an exemplary embodiment, the lenses of laser 30 are modular such that a first lens may be interchanged with a second lens.

Referring still to FIGS. 1-3 and 7-9, paddles 32 extend from body 28 and are aligned with output 36 projected by laser 30. Paddles 32 are configured to fit within cut slots 18, 18a-18d to securely attach cut plane indicator 26 to cut guide 10. When paddles 32 are received in one of slots 18, 18a-18d, laser 30 is aligned with the cut plane of that slot. For instance, as illustrated in FIG. 1, when paddles 32 are positioned in cut slot 18, laser 30 and output 36 projected by laser 30 are aligned along cut plane P of cut guide slot 18. Accordingly, laser 30 projects output 36 through slot 18 along cut plane P.

Figure 10:
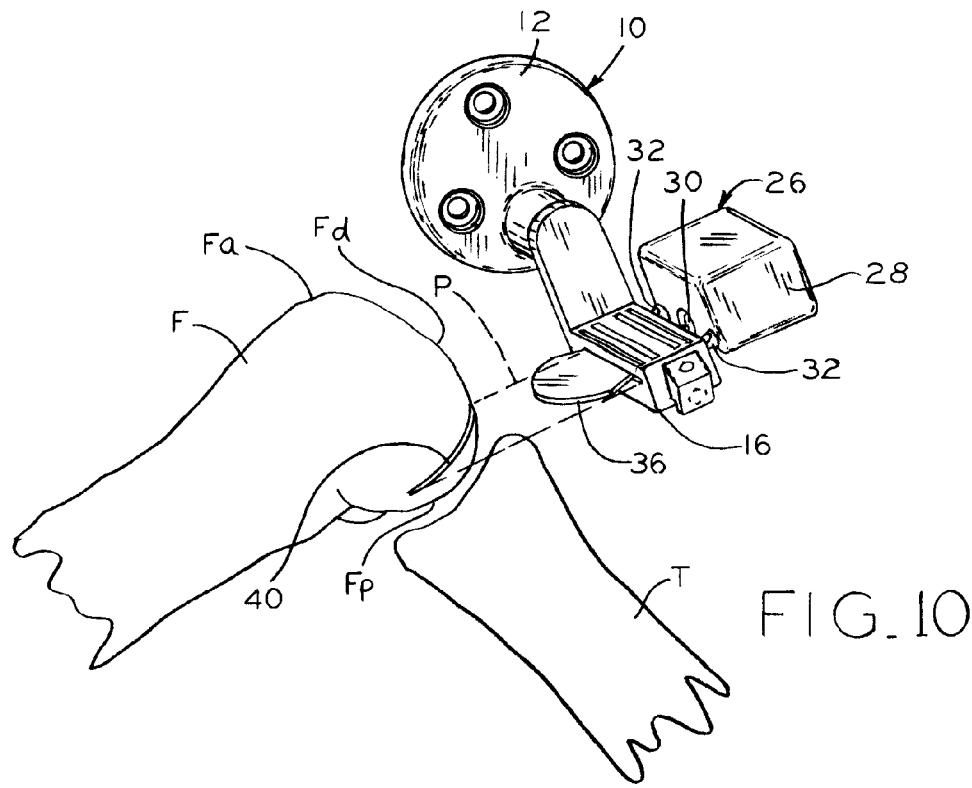
FIG. 10 is a perspective view of the cut guide and cut plane indicator device positioned to guide a first cut of a femur during a knee arthroplasty procedure.
Figure 11:
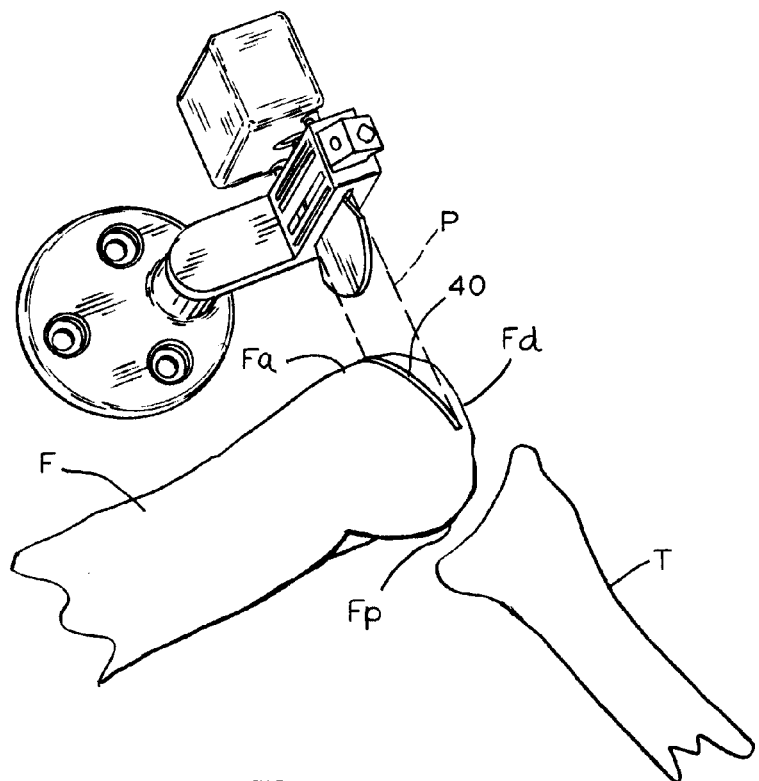
FIG. 11 is another perspective view of the cut guide and cut plane indicator device positioned to guide a second cut of a femur during a knee arthroplasty procedure.

Referring now to FIGS. 3 and 10-11, operation of the cut guide 10/cut plane indicator device 26 assembly will now be described. Cut guide 10 and cut plane indicator device 26 cooperate to facilitate the resection of the surface of a bone in preparation to receive a prosthetic implant. For instance, cut guide 10 and cut plane indicator device 26 may be used to prepare the bones of the knee joint during a knee arthroplasty procedure.

As shown in FIGS. 10 and 11, the knee joint generally includes tibia T and femur F. Femur F has distal end $F_d$, posterior side $F_p$ and anterior side $F_a$, each of which may require cutting during the procedure in order to prepare femur F to receive the pre-selected implant. To make the cut of posterior side $F_p$, the CAS system to which cut guide 10 may be attached moves cut guide 10 into position such that cut guide 10 is spaced from distal end $F_d$ of femur F but cut plane P of cut slot 18 is properly positioned in the pre-determined cut plane to guide the cut of posterior side $F_p$. The CAS system may use any known methods for determining and effecting the proper placement of cut plane P. Such methods may include first performing known preliminary-operation (pre-op) planning procedures to determine the appropriate size of implant. Pre-op procedures may include obtaining measurements of and/or producing a 3-dimensional model of the patient's femur from CT scans, x-rays, or other known methods. The CAS surgery methods may also employ a haptic device or probe, which touches femur F and obtains coordinates from which a 3-dimensional representation of femur F can be created. The CAS system may use parameters for the pre-selected implant and the coordinates of femur F to calculate the cut planes of the cuts to be made to femur F. Some of these pre-op procedures are described in U.S. patent application Ser. No. 11/610,728, entitled AN IMAGELESS ROBOTIZED DEVICE AND METHOD FOR SURGICAL TOOL GUIDANCE, incorporated by reference above.

Cut plane indicator device 26 may be coupled to cut guide 10 by inserting paddles 32 into cut slot 18, as illustrated in FIG. 3. As shown in FIG. 10, laser 30 projects output 36 through slot 18 along cut plane P and onto distal end $F_d$ of femur F to produce cut plane indicator line 40. Cut plane indicator line 40 provides the surgeon with a visual indication or cue indicating the location of the cut of posterior side $F_p$ of femur F. At this point, the surgeon can decide whether the depth, angle, and position of cut plane P and/or the initial implant size selection are appropriate. If appropriate, the surgeon may proceed to cut posterior side $F_p$ of femur F by disengaging cut plane indicator device 26 from cut guide 10 and instructing the CAS system to move cut guide 10 closer to and/or against distal end $F_d$ of femur F while maintaining cut plane P in the same orientation relative to femur F. The CAS system may be adapted to fix cut guide 10 to move in a single plane; therefore, the movement of cut guide 10 closer to distal end $F_d$ of femur F is directed only along cut plane P. Once cut guide 10 is in position, the surgeon may insert the cutting instrument through slot 18 and into femur F to cut posterior side $F_p$ along cut plane P. Alternatively, the surgeon may leave cut plane indicator device 26 engaged with cut guide 10 and may use laser line 40 as a guide to free-hand cut posterior side $F_p$ of femur F. The surgeon may also inspect the accuracy of the resulting cut surface by projecting laser output 36 across the cut surface. Laser output 36 would then reveal and indicate any areas lying above the cut plane that may have been missed by the saw.

Turning now to FIG. 11, cut plane indicator device 26 may be similarly used to verify the angle, position and depth of cut plane P when making a cut of distal end $F_d$ of femur F. The CAS system moves cut block 16 into a position such that cut block 16 is spaced from femur F but cut plane P is properly positioned on a pre-determined cut plane to guide the cut of distal end $F_d$. In this position, laser 30 (FIG. 10) of cut plane indicator device 26 projects line 40 onto anterior surface $F_a$ of femur F. Line 40 provides the surgeon with a visual indication or cue indicating the location of the cut on anterior surface $F_a$. From viewing line 40, the surgeon can decide whether the depth, angle, and position of cut plane P are appropriate. If cut plane P is appropriate, line 40 may then be used to guide the surgeon in making a free-hand cut of distal end $F_d$ if so desired. Otherwise, cut plane indicator device 26 may be removed from cut block 16, cut block 16 may be moved closer to femur F, and cut slot 18 (FIG. 10) can be used to guide the saw in making the cut of $F_d$. This procedure may be repeated for all of the necessary cuts of femur F.

Figure 7:
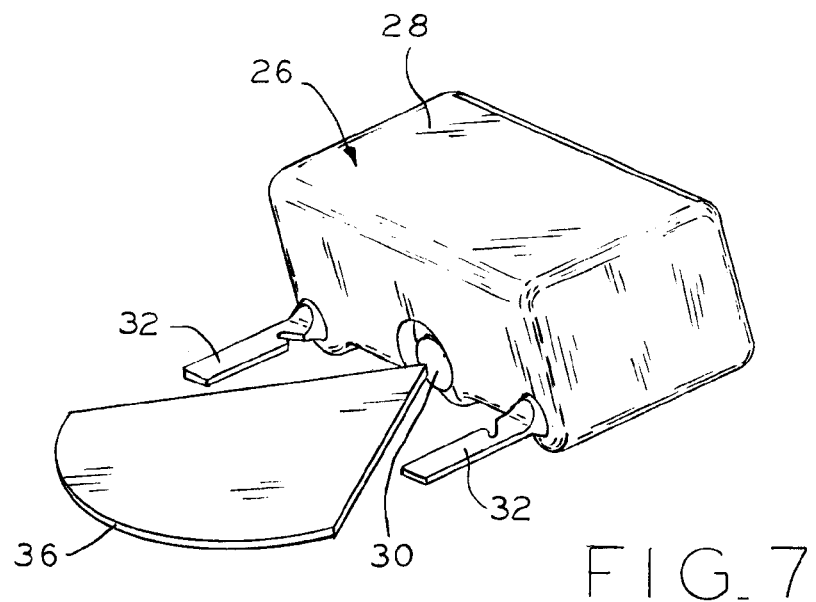
FIG. 7 is a perspective view of the cut plane indicator device of FIG. 1.
Figure 8:
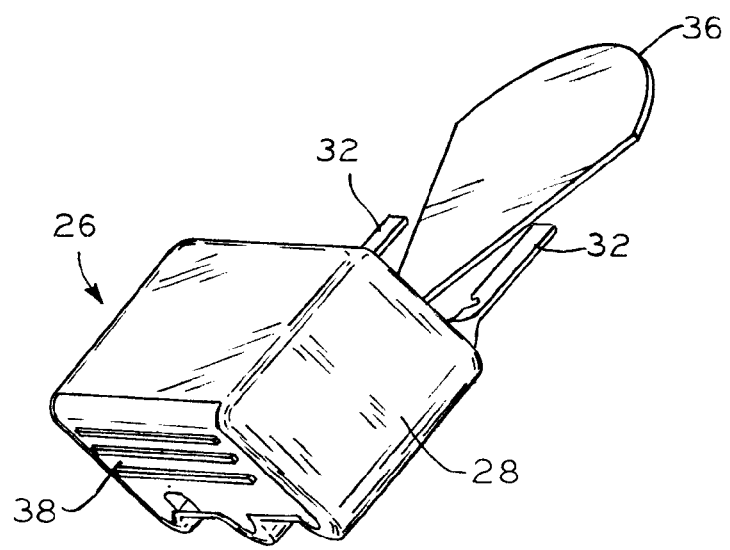
FIG. 8 is another perspective view of the cut plane indicator device of FIG. 7.
Figure 9:
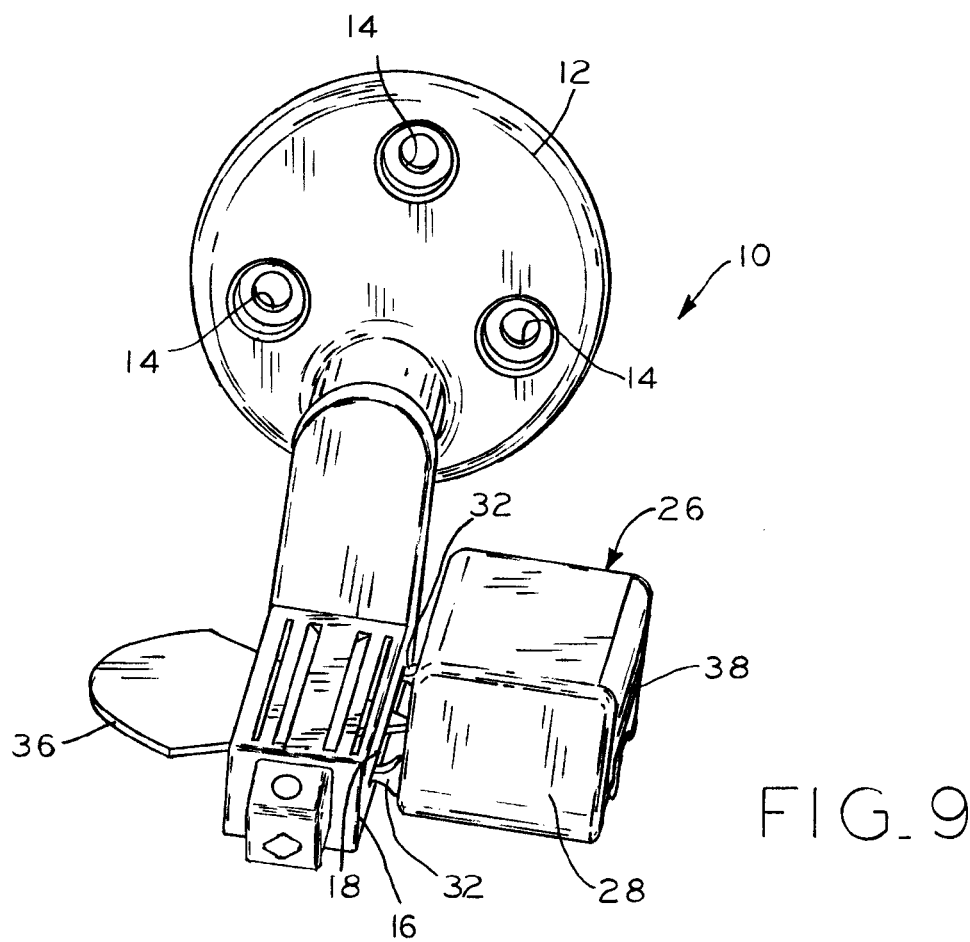
FIG. 9 is another perspective view of the cut guide and cut plane indicator device of FIG. 1.
Figure 12:
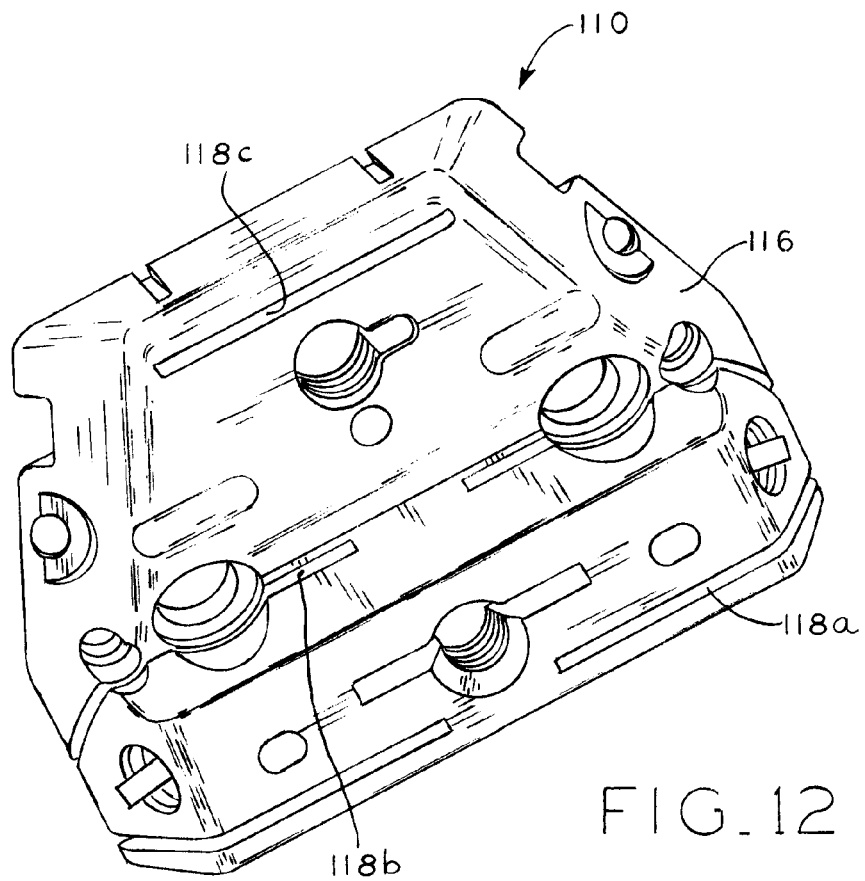
FIG. 12 is a perspective view of another cut guide with which the cut plane indicator device of FIG. 7 may be used.

It should be understood that cut plane indicator device 26 may be used with alternative existing cut guides and cut blocks, including those designed to be used manually rather than with a CAS system. For instance, FIG. 12 illustrates known femoral finishing guide 110, such as the NEXGEN Femoral Finishing Guide, available from Zimmer, Inc. of Warsaw, Ind., for example, which includes cut block 116 and a plurality of cut guide slots 118a-118c extending through cut block 116. Referring to FIGS. 7-8 and 12, paddles 32 of cut plane indicator device 26 may be inserted into any one of slots 118a-118c in a manner similar to that described above with respect to cut guide 10. In this position, laser output 36 projected by laser 30 extends through the slot and projects a line along the plane of the slot. Other examples of femoral cut guides with which cut plane indicator device 26 may be used include those guides disclosed in U.S. Patent Application Publication No. 2004/0153066, incorporated by reference above; and U.S. Patent Application Publication No. 2006/0200158, entitled APPARATUSES AND METHODS FOR ARTHROPLASTIC SURGERY, filed on Jan. 27, 2006, assigned to the assignee of the present application, the disclosure of which is hereby expressly incorporated herein by reference.

Figure 13:
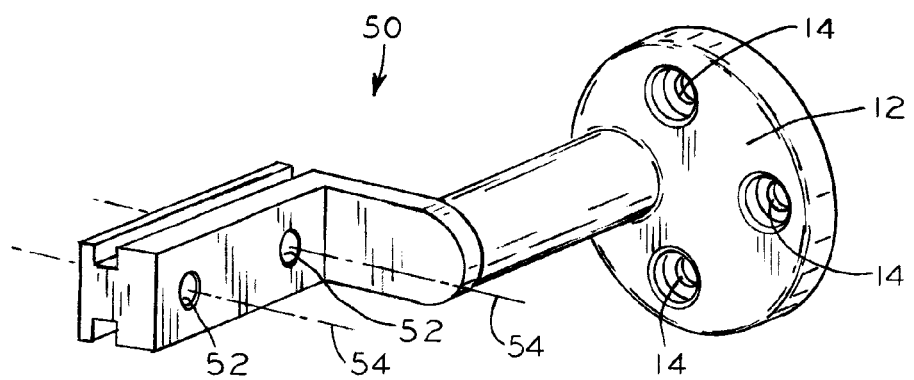
FIG. 13 is a perspective view of a drill guide.

The examples above illustrate cut plane indicator device 26 being used with femoral cut guides. However, it should be understood that the use of cut plane indicator device 26 is not limited to this particular use. Rather, cut plane indicator device 26 may be used with any cut guide, including tibial cut guides such as, for example, those disclosed in U.S. Patent Application Publication No. 2006/0200158, incorporated by reference above; and U.S. patent application Ser. No. 11/343, 849, entitled TIBIAL CUT GUIDE ASSEMBLY HAVING ROTATABLE CUT GUIDE BODY, filed on Jan. 31, 2006, assigned to the assignee of the present application, the disclosure of which is hereby expressly incorporated herein by reference. As noted, cut plane indicator device 26 may be adapted for use with any cut guide and, therefore, is also not limited to use with cut guides for knee arthroplasty. Moreover, indicator device 26 may also be adapted to be used with a drill guide. For example, laser 30 of indicator device 26 may be a point laser such that, when oriented to have a laser output extend through a drill guide, the laser output provides a reference point on an anatomical structure which may be used to guide a surgeon during a drilling procedure. FIG. 13 shows an exemplary drill guide 50 including drill guide throughbores 52 through which a laser may be oriented to project an output aligned along drill axis 54 onto an anatomical structure.

In one method for surgery on an anatomical structure according to an exemplary embodiment of the present disclosure, cut guide 10 may be attached to a robotic device, such as the BRIGIT system via adapter portion 12. The BRIGIT system may be used to obtain a plurality of landmarks on the anatomical structure to provide guidance, such as a frame of reference relative to the patient, for the BRIGIT system. The robotic device may then be switched to a free state in which a user, such as a surgeon, may freely manipulate an arm of the device to which cut guide 10 is attached and manually position cut guide 10, with cut plane indicator device 26 attached thereto, proximate the anatomical structure. Indicator source 30 of device 26 provides an indicator on the anatomical structure which identifies the location and/or depth of alteration to be accomplished with the current position of cut guide 10, i.e., indicator source 30 provides an initial alignment of cut guide 10 relative to the anatomical structure. The surgeon manually may initially position cut guide 10 based on prior experience or knowledge, similar to positioning methods for conventional cut guides. An alignment rod may be positioned substantially perpendicular to cut guide 10 and aligned with a femoral head and an ankle in an exemplary embodiment wherein the anatomical structure is a femur. The alignment rod may be substantially similar to the alignment rod described in U.S. Pat. No. 7,094,241, entitled METHOD AND APPARATUS FOR ACHIEVING CORRECT LIMB ALIGNMENT IN UNICONDYLAR KNEE ARTHROPLASTY, issued Aug. 22, 2006, assigned to the assignee of the present disclosure, the disclosure of which is hereby expressly incorporated herein by reference. Aligning the alignment rod with the femoral head and the ankle provides an indication to the surgeon that the cut guide 10 is correctly positioned. Cut guide 10 may be manually rotated until such alignment is achieved. The robotic device then is instructed to hold the current position of cut guide 10 and the alignment rod may be removed. The robotic device may then be used by the surgeon to provide small adjustments for such factors as varus/valgus, resection level, and flexion/extension adjustment. The surgeon may then use the robotic device to lock cut guide 10 into a final position after which the resection may be completed, as described above.

The embodiments illustrated and described above show cut plane indicator device 26 as a separate device removable from the cut block and usable with a variety of different cut blocks. The present disclosure also contemplates an embodiment wherein the cut plane indicator device is built into the cut block. In this case, the cut plane indicator device would include a laser housed within an opening in the cut block and aligned along the cut plane of a slot of the cut block.

In one embodiment, laser 30 of indicator device 26 may be used as a device used for overall limb alignment. For example, a surgeon or other user may use indicator device 26 as a leg alignment device. The surgeon may position laser 30 proximate a hip joint of a patient and orient output 36 of laser 30 to assess whether a femoral head, a knee joint, and an ankle joint of the patient are properly aligned.

While this disclosure has been described as having exemplary designs, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A guidance system for guiding a surgical procedure performed on an anatomical structure, the guidance system comprising:
   a surgical guide instrument including a cut block comprising a plurality of interconnected exterior surfaces and adapted to be positioned proximate the anatomical structure, at least two of the exterior surfaces interconnecting along a longitudinal straight edge, said guide instrument having at least one cut guide slot defined by an aperture extending longitudinally in a first direction parallel to the longitudinal straight edge along at least one of the exterior surfaces of the cut block, the at least one cut guide slot further spanning through the cut block between opposed exterior surfaces along a guide direction being transverse to the first direction so as to define a cut plane; and
   a light-emitting device securable to said guide instrument in a secured position such that an output of said light-emitting device is projected through said at least one longitudinal cut guide slot of the cut block and along said guide direction, the output of said light-emitting device circumscribed by the at least one cut guide slot to form a linear projection on the anatomical structure to indicate an illuminated cut plane.

2. The guidance system of claim 1, wherein said light-emitting device comprises a laser.

3. The guidance system of claim 2, wherein said laser comprises a line-projecting laser.

4. The guidance system of claim 2, wherein said light-emitting device further comprises a lens.

5. The guidance system of claim 2, wherein the output of the laser is substantially fan-shaped.

6. The guidance system of claim 1, wherein said light-emitting device is integrally formed with said guide instrument.

7. The guidance system of claim 1, wherein the light-emitting device is supported by a housing which is removably coupled to the guide instrument.

8. The guidance system of claim 7, wherein said housing and said guide instrument cooperate to align the output of the light-emitting device with the cut plane.

9. The guidance system of claim 8, wherein, said housing includes alignment tabs configured to receive said guide instrument such that said housing is positionable along said at least one longitudinal cut guide slot.

10. The guidance system of claim 1, wherein said guide instrument is operably coupled to a computer assisted surgery system.

11. The guidance system of claim 1, further comprising a plurality of cut guide slots having apertures, at least one aperture extending longitudinally along a first exterior surface and further spanning through the cut block between opposed exterior surfaces, and at least another aperture extending longitudinally along a separate second exterior surface and further spanning through the cut block between opposed exterior surfaces.

12. A guidance system for guiding a surgical procedure performed on an anatomical structure, the guidance system comprising:
   guidance means for guiding a surgical instrument relative to a guide direction, said guidance means including at least one cut guide slot having an aperture extending longitudinally in a first direction along at least one of a plurality of interconnected exterior surfaces of a cut block, at least two of the exterior surfaces interconnecting along a longitudinal straight edge being parallel to the first direction, the at least one cut guide slot further spanning through the cut block between opposed exterior faces along the guide direction, the guide direction being transverse to the first direction and defining a cut plane through the cut block; and
   light indication means for providing a linear indicator on the anatomical structure circumscribed by the at least one cut guide slot and corresponding to said cut plane.

13. The guidance system of claim 12, wherein said indication means comprises a light-emitting device.

14. The guidance system of claim 12, further comprising alignment means for aligning said indication means relative to said guidance means.

15. The guidance system of claim 12, further comprising computer means for providing computer assisted guidance to the guidance system.

* * * * *